(12) United States Patent
Blacker et al.

(10) Patent No.: US 8,865,924 B2
(45) Date of Patent: Oct. 21, 2014

(54) COMPOUNDS FOR USE AS LIGANDS

(71) Applicants: John Blacker, Leeds (GB); Kevin Treacher, Manchester (GB); Thomas Screen, Manchester (GB)

(72) Inventors: John Blacker, Leeds (GB); Kevin Treacher, Manchester (GB); Thomas Screen, Manchester (GB)

(73) Assignee: University of Leeds, Leeds (GB)

( * ) Notice: Subject to any disclaimer, the term of this patent is extended or adjusted under 35 U.S.C. 154(b) by 0 days.

(21) Appl. No.: 13/912,508

(22) Filed: Jun. 7, 2013

(65) Prior Publication Data
US 2013/0267725 A1 Oct. 10, 2013

Related U.S. Application Data

(63) Continuation of application No. 12/864,402, filed as application No. PCT/GB2009/050012 on Jan. 9, 2009, now Pat. No. 8,501,829.

(30) Foreign Application Priority Data

Jan. 25, 2008 (GB) .................................. 0801319.5

(51) Int. Cl.
C07F 17/02 (2006.01)
B01J 31/00 (2006.01)
B01J 31/22 (2006.01)

(52) U.S. Cl.
CPC ................................. B01J 31/2295 (2013.01); C07F 17/02 (2013.01)
USPC ............... 556/136; 556/52; 556/53; 556/137; 556/143

(58) Field of Classification Search
CPC .................................. C07F 17/02; B01J 31/00
USPC .............................. 556/136, 137, 143, 52, 53
See application file for complete search history.

(56) References Cited

U.S. PATENT DOCUMENTS

2004/0053331 A1   3/2004   Kahn et al.

FOREIGN PATENT DOCUMENTS

| WO | 03068787 | 8/2003 |
|---|---|---|
| WO | 2006010885 | 2/2006 |
| WO | 2007096592 | 8/2007 |

OTHER PUBLICATIONS

Simal et al., Journal of Organometallic Chemistry, vol. 558, No. 1-2, pp. 163-170 (1998).*
Barišićet al., Journal of Organometallic Chemistry, vol. 682, No. 1-2, pp. 131-142 (2003).*
Sabapathy et al., Langmuir, vol. 14, No. 1-2, pp. 124-136 (1998).*
Jutzi et al., Journal of Organometallic Chemistry, vol. 498, pp. 127-137 (1995).*
Holle et al., Journal of Organometallic Chemistry, vol. 605, pp. 157-167 (2000).*
Hitchcock et al., Journal of Organometallic Chemistry, vol. 669, pp. 101-105 (2003).*
Jutzi et al., Organometallics, vol. 13, No. 10, pp. 3854-3861 (1994).*
Oberbeckmann et al., Organometallics, vol. 20, No. 15, pp. 3265-3273 (2001).*
Hanasaka et al., Organometallics, vol. 25, No. 19, pp. 4643-4647 (2006).*
Chu et al., Organometallics, vol. 17, No. 13, pp. 2768-2777 (1998).*
Lindsell et al. "Investigations of Benzyl and Aryl Palladium Complexes with Pendant Hydroxy Substituents and Their Transformation into Benzolactones on Carbonylation", Organometallics 2005, vol. 24, p. 1119-1133.
Jankowiak et al. "1,1'-Bis(3-hydroxypropyl)ferrocene: Preparation and Substitution with Polyfluoroalkyl Groups", Inorganica Chimica Acta 2007, vol. 360, p. 3637-3641.
Bergert et al. "Catalysis by Titanocene-Functionalized Polymer-Supported Dendrimers", Tetrahedron Letters 2007, vol. 48, p. 8101-8103.
Schumann et al. "Synthesis, Immobilization and Catalytic Activity of Some Silylated Cyclopentadienyl Rhodium(I) Complexes", Inorganica Chimica Acta 1998, vol. 280, p. 21-25.
Yu et al. "Preparation of Polymer-Supported Phosphine from Ferrocene for palladium-catalyzed Suzuki-Miyaura Cross-Coupling Reactions", Chinese Chemical Letters 2007, vol. 18, p. 37-40.
International Search Report for PCT/GB2009/050012, Completed by the European Patent Office on Apr. 1, 2009, 6 Pages.
Blacker, A.J. et al., "A Low-Waste Process to Sertraline by Diasteromeric Crystal Resolution and Waste Isomer Racemisation," Organic Proc. Research & Dev. 2009, 13, pp. 1370-1378.
Brtovsek, G.J.P. et al., "The Search for New-Generation Olefin Polymerization Catalysts: Life Beyond Metallocenes," Angew. Chem. Int. Ed. 1999 38, pp. 428-447.
Britovsek, G.J.P. et al., "The Search for New-Generation Olefin Polymerization Catalysts: Life Beyond Metallocenes," Angew. Chem. Int. Ed. 1999 38, pp. 428-447.

* cited by examiner

*Primary Examiner* — Porfirio Nazario Gonzalez
(74) *Attorney, Agent, or Firm* — Brooks Kushman P.C.

(57) ABSTRACT

The present invention relates to compounds and their use as ligands, in particular, in metal catalyst complexes. The ligands of the invention are capable of binding to a solid support. The invention includes the ligands in their own right and when bound to a support and the compounds may be used to prepare metal catalyst complexes.

17 Claims, 1 Drawing Sheet

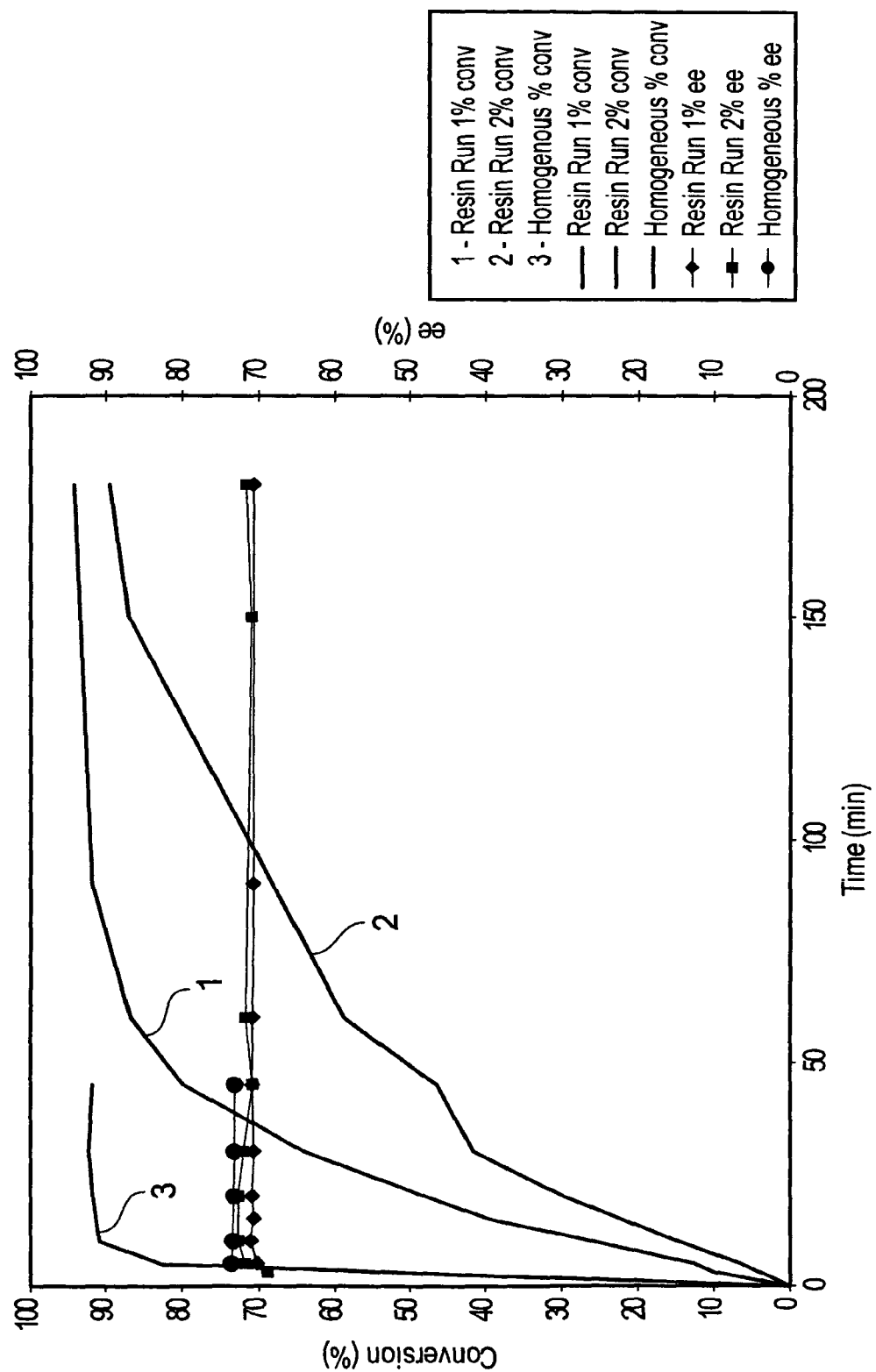

COMPOUNDS FOR USE AS LIGANDS

CROSS REFERENCE TO RELATED APPLICATIONS

This application is a continuation of U.S. Ser. No. 12/864,402 filed Jul. 23, 2010, issued as U.S. Pat. No. 8,501,829 on Aug. 6, 2013, which is the U.S. national phase of PCT Appln. No. PCT/GB2009/050012 filed Jan. 9, 2009, which claims priority from Great Britain Appln. No. 0801319.5 filed Jan. 25, 2008, the disclosures of which are hereby incorporated in their entirety by reference herein.

FIELD OF THE INVENTION

This invention relates to compounds and their use as ligands, in particular in metal catalyst complexes. More specifically, the invention is concerned with ligands that are capable of binding to a solid support. The invention includes the ligands in their own right and when bound to a support. The ligands are used to prepare metal catalyst complexes which are easy to recover. This feature aids catalyst recycling and also facilitates their use in flow processing. These features lead in turn to improved efficiency and output.

BACKGROUND TO THE INVENTION

Many homogeneous catalysts are based on organometallic complexes, in particular complexes comprising transition metals. Organometallic complexes comprising η-cyclopentadienyl ligands are particularly useful. This class of electron-rich aromatic ligand is often strongly bound to the metal catalyst, resulting in stable complexes with significant steric bulk around the metal centre. The pentamethylcyclopentadienyl (Cp*) ligand is commonly used in conjunction with transition metal catalysts such as Ru, Rh, Ir, Ti and Fe. Although many benefits may be derived from such catalysts, the catalysts are expensive and therefore may need to be recovered at the end of a reaction to enable economic use. Homogeneous catalysts are, however, often difficult to separate from the product in a simple and economical fashion. To address these limitations, attempts have been made to prepare cyclopentadienyl ligands which are bound to a solid support. However, many of these processes require a complex multi-step synthesis to produce the desired ligands.

WO 2007/096592 discloses a microencapsulated catalyst-ligand system comprising a polymeric ligand encapsulated within a permeable polymer shell. This publication discloses inter alia the encapsulation of cyclopentadienyl ligands, including 1-(3-hydroxypropyl)-2,3,4,5-tetramethylcyclopentadiene, 1-(4-hydroxybutyl)-2,3,4,5-tetra methylcyclopentadiene, 1-(5-hydroxypentyl)-2,3,4,5-tetramethylcyclopentadiene, 1-(3-aminopropyl)-2,3,4,5-tetramethylcyclopentadiene, 1-(4-aminobutyl)-2,3,4,5-tetramethyl cyclopentadiene, 1-(5-aminopentyl)-2,3,4,5-tetramethylcyclopentadiene and 1-(8-hepta decenyl)-2,3,4,5-tetramethylcyclopentadiene.

SUMMARY OF THE INVENTION

The present invention provides ligands, including without limitation cyclopentadienyl ligands, which are capable of binding to a solid support. The solid supported catalysts produced in accordance with the invention have a number of benefits including improved metal recovery, reduced metal contamination of reaction products, simpler product purification and the potential for catalyst recycling. In addition, the immobilised catalysts allow reactions to be run under flow conditions rather than under batch conditions, which provides a number of benefits in processing terms.

A further benefit of the catalysts is that the ligand environment around the metal centre is well defined in the supported metal catalyst. This is a significant advantage relative to microencapsulated catalysts.

According to a first aspect of the present invention, there is provided a compound of the formula (I):

wherein
  $R^1$ is an unsaturated carbocyclic group having five or six ring carbon atoms;
  X is a linker comprising at least two in-chain carbon atoms; and
  Y is selected from =O, =S, —OH, —SH, —S(O), —S(O)$_2$, amino and monosubstituted amino.

In a further aspect, the invention provides supported compounds of the formula (II):

wherein
  $R^1$ and X are as defined in formula (I);
  Y' is selected from —O—, —S— and aminylene; and
  Z is a support.

Also provided are metal complexes comprising, as a ligand, a compound of formula (I) or a compound of formula (II). Metal complexes of the invention may comprise a metal catalyst, for example a transition metal catalyst. Processes for the production of compounds of the invention and metal complexes thereof are also provided.

Compounds of the invention may be used to prepare metal catalyst complexes which are readily recoverable and which have desirable catalytic activity. The resulting metal catalysts may be used to catalyse a variety of reactions, for example transfer hydrogenation, dehydrogenation, metathesis or polymerisation processes. Furthermore, the compounds may be prepared from inexpensive and readily available starting materials via a limited number of processing steps.

DESCRIPTION OF VARIOUS EMBODIMENTS

In formulae (I) and (II), $R^1$ is an unsaturated carbocyclic group having five or six ring carbon atoms. The carbocyclic group may be unsubstituted or substituted by one or more (e.g. 1, 2, 3, 4 or 5) substituents. Exemplary substituents include optionally substituted hydrocarbyl groups, e.g. optionally substituted $C_{1-20}$ alkyl (e.g. $C_1$, $C_2$, $C_3$ or $C_4$ alkyl), terpenes (e.g. menthyl, neomenthyl or limonenyl) or optionally substituted aryl (e.g. phenyl) groups.

In a preferred embodiment, $R^1$ is an unsaturated carbocyclic group having five ring carbon atoms. In a particular embodiment, $R^1$ is a cyclopentadienyl group. The cyclopentadienyl group may be unsubstituted or substituted with 1, 2, 3 or 4 substituents. The substituents may be independently chosen. Exemplary substituents include optionally substituted hydrocarbyl groups, for example selected from optionally substituted $C_{1-20}$ alkyl (e.g. $C_1$, $C_2$, $C_3$ or $C_4$ alkyl), terpenes (e.g. menthyl, neomenthyl or limonenyl) and optionally substituted aryl (e.g. phenyl) groups. In one embodiment, $R^1$ is cyclopentadienyl optionally substituted with 1, 2, 3 or 4 substituents independently selected from methyl, ethyl and phenyl. In another embodiment, $R^1$ is cyclopentadienyl optionally substituted with 1, 2, 3 or 4 methyl groups. In a further embodiment, $R^1$ is tetramethylcyclopentadienyl. The cyclopentadienyl group may be present in the form of one or more structural isomers, each of which is encompassed by the present invention. The cyclopentadienyl group may be in the form of a deprotonated anion and therefore may comprise a cationic counterion.

In another embodiment, $R^1$ is an unsaturated carbocyclic group having six ring carbon atoms. The carbocyclic group may be aromatic or non-aromatic; preferably it is an aromatic group. Examples include phenyl and naphthyl groups. Included are compounds in which $R^1$ is a phenyl group. The phenyl group may be unsubstituted or substituted with 1, 2, 3, 4 or 5 substituents. Exemplary substituents include optionally substituted hydrocarbyl groups, for example selected from optionally substituted $C_{1-20}$ alkyl (e.g. $C_1$, $C_2$, $C_3$ or $C_4$ alkyl), terpenes (e.g. menthyl, neomenthyl or limonenyl) and optionally substituted aryl (e.g. phenyl) groups.

The linker X comprises at least two in-chain carbon atoms. Typically, X is acyclic. In embodiments, each of the in-chain atoms of X is independently selected from carbon, nitrogen, oxygen and sulphur.

In certain compounds, X is a hydrocarbylene linker optionally interrupted by one or more (e.g. 1, 2, 3 or 4) in-chain heteroatoms, e.g. selected from oxygen, nitrogen and sulphur. In other compounds, X is a hydrocarbylene linker. The term "hydrocarbylene" as used herein refers to a linker having a chain consisting exclusively of hydrogen and carbon atoms, wherein the chain may be unsubstituted or substituted with one or more (e.g. 1, 2, 3, 4 or 5) substituents. In one embodiment, X is a hydrocarbylene linker having from 2 to 20 (e.g. from 2 to 10) in-chain carbon atoms. Where the hydrocarbylene chain is substituted, the one or more substituents may, for example, be selected from amino, hydroxy, $C_{1-6}$ alkyl, $C_{1-6}$ alkoxy, carbonyl, carbocyclyl (e.g. aryl or $C_{3-6}$ cycloalkyl) and heterocyclyl (e.g. heteroaryl) groups.

In one embodiment, X is an alkylene group or an alkenylene group, either of which is optionally interrupted by one or more (e.g. 1, 2, 3 or 4) in-chain heteroatoms. The term "alkylene" in this context refers to a divalent, straight or branched chain alkane group which is optionally substituted with one or more (e.g. 1, 2, 3, 4 or 5) substituents. "Alkenylene" refers to an alkylene group having at least one double bond, of either E or Z stereochemistry where applicable. In embodiments, X is an alkylene or alkenylene group, e.g. having from 2 to 20 (e.g. from 2 to 10) in-chain carbon atoms. Exemplary alkylene groups include ethylene, propylene (e.g. n-propylene), butylene (e.g. n-butylene) and pentylene (e.g. n-pentylene), any of which is optionally substituted with one or more (e.g. 1, 2, 3, 4 or 5) substituents. Exemplary alkenylene groups include ethenylene, 2-propenylene, 1-butenylene, 2-butenylene, 3-butenylene, 1-pentenylene, 2-pentenylene and 3-pentenylene, any of which is optionally substituted with one or more (e.g. 1, 2, 3, 4 or 5) substituents. Where the alkylene or alkenylene chain is substituted, the one or more substituents may, for example, be selected from amino, hydroxy, $C_{1-6}$ alkyl, $C_{1-6}$ alkoxy, carbonyl, carbocyclyl (e.g. aryl or $C_{3-6}$ cycloalkyl) and heterocyclyl (e.g. heteroaryl) groups.

In formula (I), Y is selected from =O, =S, —OH, —SH, —S(O), —S(O)$_2$, amino and monosubstituted amino. Where Y is monosubstituted amino, the amino group may be substituted with, for example, an optionally substituted hydrocarbyl group (e.g. a $C_{1-6}$ alkyl, aryl or arylalkyl group), a heterocyclyl group (e.g. a heteroaryl group) or a heterocyclylalkyl group, any of which is optionally attached to the nitrogen atom of the amino group via a linkage selected from —O—, —C(O)— —C(O)O—, —S—, —S(O)— and —S(O)$_2$—. Exemplary monosubstituted amino groups include N—($C_{1-6}$ alkyl)amino, acetylamino and tosylamino groups. In one embodiment, Y is selected from =O, —OH and —NH$_2$.

In formula (II), Y' is selected from —O—, —S— and aminylene. The term "aminylene" as used herein refers to an optionally substituted, divalent amine group. Included are compounds in which Y' is —NH— optionally substituted with a hydrocarbyl group (e.g. a $C_{1-6}$ alkyl, aryl or arylalkyl group), a heterocyclyl group (e.g. a heteroaryl group) or a heterocyclylalkyl group, any of which is optionally attached to the nitrogen atom of the aminylene group via a linkage selected from —O—, —C(O)— —C(O)O—, —S—, —S(O)— and —S(O)$_2$—. Exemplary aminylene groups include —NH—, —N($C_{1-6}$ alkyl)-, —N(acetyl)- and —N(tosyl)-groups. In one embodiment, aminylene is —NH—.

In a particular embodiment, the invention provides compounds of formula (I) in which —X—Y is selected from 2-hydroxyethyl, 3-hydroxy-n-propyl, 4-hydroxy-n-butyl, 5-hydroxy-n-pentyl, 2-hydroxypropyl, 3-hydroxybutyl, 3-hydroxy-1-methylpropyl, 1-methylene-3-hydroxypropyl, 3-hydroxyprop-1-enyl, 3-hydroxy-3-phenylpropyl, 2-oxopropyl, 3-oxobutyl, 4-oxopentyl, 3-aminopropyl, 5-aminopentyl, 3-propanoate and 5-pentanoate. Also provided are compounds of the formula (II) derived by reacting said compounds of formula (I) with a solid support.

In another embodiment, the compound of formula (I) is not selected from 1-(3-hydroxypropyl)-2,3,4,5-tetramethylcyclopentadiene, 1-(4-hydroxybutyl)-2,3,4,5-tetra methylcyclopentadiene, 1-(5-hydroxypentyl)-2,3,4,5-tetramethylcyclopentadiene, 1-(3-aminopropyl)-2,3,4,5-tetramethylcyclopentadiene, 1-(4-aminobutyl)-2,3,4,5-tetramethyl cyclopentadiene, 1-(5-aminopentyl)-2,3,4,5-tetramethylcyclopentadiene and 1-(8-hepta decenyl)-2,3,4,5-tetramethylcyclopentadiene.

A compound of formula (II) may be obtained by reacting a compound of formula (I) with a support, e.g. a solid support, containing one or more functionalities which are capable of reacting with the moiety Y. Suitable supports and methods of attachment will be familiar to those skilled in the art. For example, where Y is oxo or thioxo, a support comprising one or more pendant amine functionalities may be employed. Where Y is hydroxy, a support comprising one or more pendant carboxylic acid or halogen groups may advantageously be used. Typically, the resulting compound will be bound to an outer surface of the support, e.g. to the surface of a polymer bead.

Supports include inorganic supports and organic supports, particularly polymer supports. In embodiments, the support is a solid support.

Inorganic supports may be derived from naturally occurring inorganic materials or matrices or may be synthesised. Inorganic materials or matrices include glasses, silicas, aluminas, titanates and hybrid oxides thereof, graphites, oxides and zeolites.

Polymer supports may be derived from the polymerisation of a composition comprising one or more monomers, and are preferably derived from the polymerisation a composition comprising of two or more monomers. The monomers may contain one or more polymerisable double bonds. In one embodiment, the polymer support is derived from the polymerisation of a composition comprising one or more monomers containing only one polymerisable double bond, and one or more monomers containing two or more polymerisable double bonds. In another embodiment, the polymer support is derived from the polymerisation of a composition comprising one or two monomers containing only one polymerisable double bond, and one monomer containing two or three polymerisable double bonds. Examples of monomers containing only one polymerisable double bond include styrene and substituted styrenes such as a-methyl styrene, methyl styrene, t-butyl styrene, bromo styrene and acetoxy styrene; alkyl esters of mono-olefinically unsaturated dicarboxylic acids such as di-n-butyl maleate and di-n-butyl fumarate; vinyl esters of carboxylic acids such as vinyl acetate, vinyl propionate, vinyl laurate and vinyl esters of versatic acid such as VeoVa 9 and VeoVa 10 (VeoVa is a trademark of Shell); acrylamides such as methyl acrylamide and ethyl acrylamide; methacrylamides such as methyl methacrylamide and ethyl methacrylamide; nitrile monomers such as acrylonitrile and methacrylonitrile; and esters of acrylic and methacrylic acid, preferably optionally substituted $C_{1-20}$ alkyl and $C_{1-20}$ cycloalkyl esters of acrylic and methacrylic acid, such as methyl acrylate, ethyl acrylate, n-butyl acrylate, 2-ethylhexyl acrylate, i-propyl acrylate, and n-propyl acrylate, methyl methacrylate, ethyl methacrylate, n-butyl methacrylate, 2-ethylhexyl methacrylate, i-propyl methacrylate, n-propyl acrylate, hydroxyethyl acrylate, hydroxyethyl methacrylate, N,N-dimethylaminoethyl acrylate and N,N-dimethylaminoethyl methacrylate. Functional derivatives of the foregoing monomers containing only one polymerisable double bond can also be employed. Examples of monomers containing two or more polymerisable double bonds include divinylbenzene (DVB), trivinylbenzene, and multifunctional acrylates and methacrylates such as ethylene glycol diacrylate, ethylene glycol dimethacrylate, trimethylolpropane triacrylate, trimethylolpropane trimethacrylate, ethylene bisacrylamide, pentaerythritol triacrylate, pentaerythritol tetraacrylate, pentaerythritol trimethacrylate, pentaerythritol tetramethacrylate and N,N-bis-acryloyl ethylene diamine.

The solid support may be a macroporous resin. The term "macroporous" indicates a class of resins which have a permanent, well developed porous structure. Importantly, these resins can have much higher surface areas (as measured by nitrogen BET) in the dry state than gel type resins. Typically, surface areas in the dry state can range from 50 to 1000 m/g. Although there is no, universally accepted definition of a macroporous resin, in the case of styrene-DVB resins it has been suggested that a macroporous resin may be defined as resin which in the dry state when exposed to cyclohexane exhibits a cyclohexane uptake of at least 0.1 mg$^{-1}$ over 16 h. Macroporous resins are often formed when the composition comprising monomers containing two or more polymerisable double bonds is polymerised in the presence of a porogen. The porogen causes phase separation of the polymer matrix. Removal of the porogen and drying yields rigid, opaque, permanently porous beads. Phase separation is controlled by the nature and level of the porogen employed, and the level of crosslinking agent employed. By way of example, the solid support may be a macroporous chloromethyl resin.

The support may comprise a poly(ethylene glycol). The use of a poly(ethylene glycol)-based support may advantageously allow compounds of the invention and metal complexes thereof to be separated from the reaction mixture, e.g. using membrane separation techniques. In embodiments, the support comprises a poly(ethylene glycol) having a number average molecular weight Mn of from about 100 to about 10000 Daltons, e.g. from about 200 to about 5000 Daltons, in particular from about 200 to about 2000 Daltons. In a particular embodiment, Z comprises a poly(ethylene glycol) and —X—Y'— is an ether or polyether chain.

The support may be in the form of one or more beads, for example one or more polymer beads. In one embodiment, the solid support comprises one or more beads having a diameter of from 10 μm to 2000 μm, e.g. from 50 μm to 1000 μm, e.g. from 75 μm to 500 μm.

Also provided is a metal complex comprising a metal, e.g. a metal catalyst, and one or more ligands, wherein at least one of the ligands is a compound of formula (I) or a compound of formula (II). Compounds of the invention will generally coordinate to the metal via the group $R^1$. A metal complex comprising a ligand of the formula (II) may be obtained by attaching a metal complex comprising a ligand of the formula (I) to a solid support via the moiety Y. Alternatively, the metal complex may be obtained by reaction of a compound of the formula (II) with a metal.

The metal complex preferably comprises a transition metal. For example, the metal may be selected from rhodium, iridium, platinum, palladium, titanium, ruthenium, cobalt and iron. Of particular mention as metals are rhodium (e.g. rhodium (III)) and iridium (e.g. iridium (III)). The metal complex typically comprises one or more additional ligands, for example selected from halogen (e.g. chloro or iodo). The metal complex may be in the form of a dimer.

The invention also provides a process for preparing a compound of the formula (I) in which $R^1$ is a cyclopentadienyl group. The process comprises contacting a compound of formula (III):

(III)

wherein

X and Y are as defined in formula (I); and each $R^2$ is independently an ethenyl group;

with an acid under conditions such that the $R^2$ groups and the carbon atom together form a cyclopentadienyl group.

Each of the ethenyl groups represented by $R^2$ may be unsubstituted or substituted. In one embodiment, each $R^2$ is ethenyl optionally substituted with 1 or 2 substituents, for example selected from optionally substituted hydrocarbyl groups. Exemplary optionally substituted hydrocarbyl substituents include optionally substituted $C_{1-20}$ alkyl (e.g. $C_1$, $C_2$, $C_3$ or $C_4$ alkyl), terpenes (e.g. menthyl, neomenthyl or limonenyl) or optionally substituted aryl (e.g. phenyl) groups. In another embodiment, each $R^2$ is ethenyl optionally substituted with 1 or 2 substituents selected from methyl, ethyl and phenyl. In a further embodiment, each $R^2$ is 1,2-dimethylethenyl. Where an ethenyl group is substituted, it may be of either E or Z stereochemistry where applicable.

The acid may be any suitable proton donor and is typically in aqueous form. By way of illustration, the acid may be aqueous hydrochloric acid.

The above process is carried out under conditions which promote formation of a cyclopentadienyl group, rather than, for example, a cyclopentenyl group. Thus, in embodiments, the process is carried out under oxidizing conditions.

In one embodiment, the process further comprises contacting the compound of formula (I) with a metal to form a metal complex of the invention. The process may further comprise attaching the resulting metal complex to a support via the moiety Y.

In an alternative embodiment, the process further comprises converting the compound of formula (I) to a compound of formula (II), by attaching the compound of formula (I) to a support via the moiety Y. The process may further comprise contacting the resulting compound of formula (II) with a metal to form a metal complex of the invention.

A compound of the formula (III) may be obtained by reacting a compound of the formula (IV):

$$R^2M \quad (IV)$$

wherein $R^2$ is as defined in formula (III) and M comprises a metal;
with a compound of the formula (V):

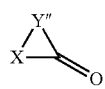
(V)

wherein X is as defined in formula (III) and Y" is —O—, —S— or aminylene.

In one embodiment, the metal M comprises magnesium or lithium. In another embodiment, M is a magnesium halide, e.g. MgBr. Typically, the compound of formula (IV) and the compound of formula (V) are contacted in an approximate molar ratio of 2 to 1.

Suitable reagents and conditions for conducting the various reactions described above are illustrated in the Examples described herein. It will be understood that the processes detailed herein are provided solely for the purpose of illustrating the invention and should not be construed as limiting. A process utilising similar or analogous reagents and/or conditions known to one skilled in the art may also be used to obtain a compound of the invention. Any mixtures of final products or intermediates obtained can be separated on the basis of the physico-chemical differences of the constituents, in a known manner, into the pure final products or intermediates.

In a particular embodiment, the compound of formula (V) is a lactone, i.e. a compound in which Y" is —O—. Exemplary lactones include the following compounds:

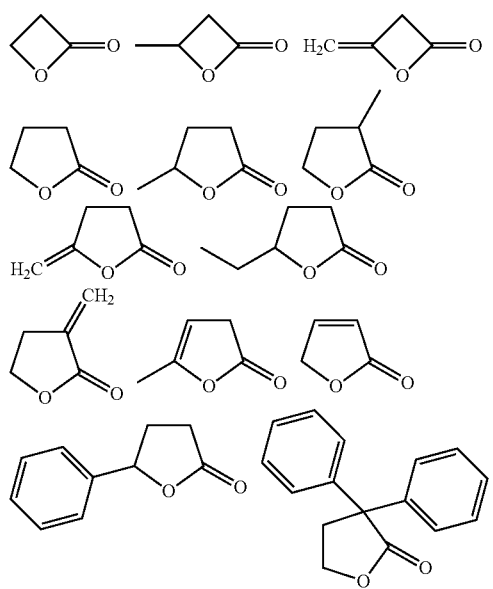

-continued

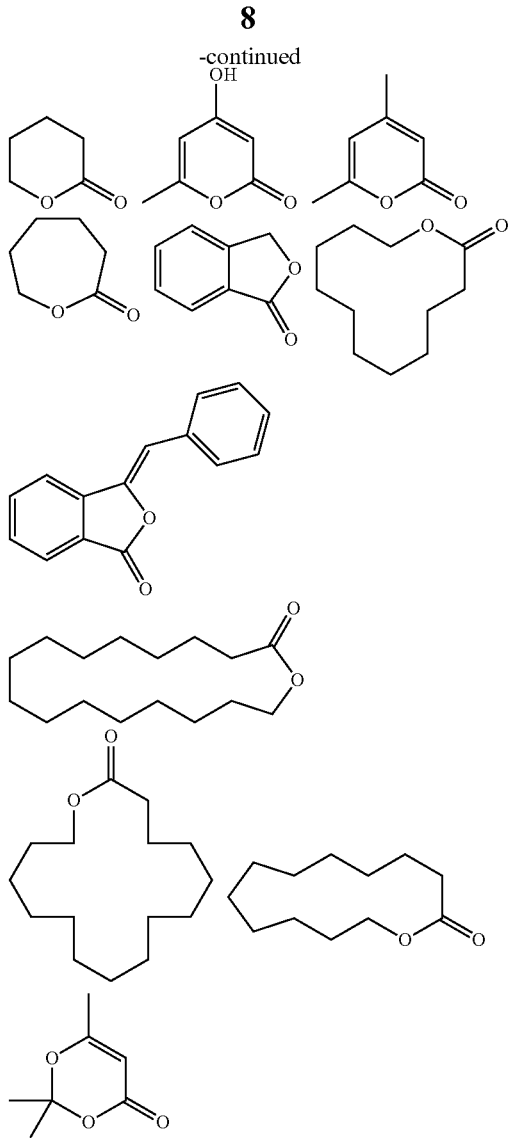

The following Examples illustrate the invention.

Example 1

1-5-Hydroxypentyl)-tetramethylcyclopentadiene (Cp*C$_5$OH)

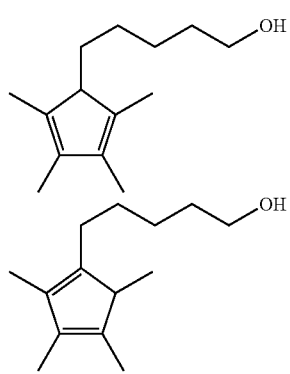

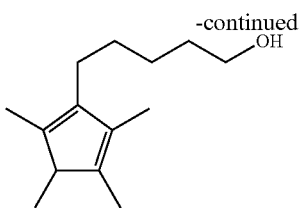
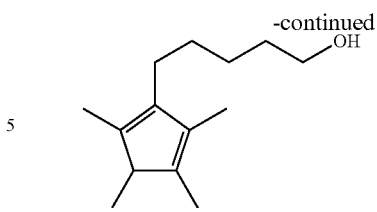

An oven dried three-necked 100 ml round bottom flask with reflux condenser and dropping funnel attached was placed under a nitrogen atmosphere then charged with anhydrous diethyl ether (15 ml). Lithium wire (0.90 g, 130 mmol, 3.2 mm diameter, 0.5-1% sodium) was washed with hexane, cut into small pieces and added to the reaction flask. 2-bromo-2-butene (6.9 ml, 67.5 mmol, mixture of cis and trans isomers) was placed in the dropping funnel and a small portion added to the vigorously stirred lithium suspension. Once reaction had initiated, evidenced by refluxing of the solvent, the remaining 2-bromo-2-butene was diluted with diethyl ether (20 ml) and added at a rate to maintain a gentle reflux. After complete addition, the reaction mixture was stirred for 1 h at r.t. Caprolactone (3.3 ml, 31.2 mmol) in diethyl ether (10 ml) was then added dropwise. After stirring for a further 30 min, the reaction mixture was poured into sat NH$_4$Cl aq (120 ml), the ether layer separated and the aqueous layer extracted with ether (2×40 ml). The combined ether layers were dried over MgSO$_4$ and concentrated to approx. 30 ml. 10% Aqueous hydrochloric acid (50 ml) was added to the concentrate and the two phase mixture stirred for 1.5 h at r.t. The ether layer was separated and the aqueous layer extracted with ether (2×30 ml). The combined ether layers were washed with water, dried over Na$_2$SO$_4$ and solvent removed to give a yellow oil. Purification by eluting through a plug of silica (heptane/EtOAc 4:1 as eluent) gave the product as a pale yellow oil (3.94 g, 61%). HPLC Retention time 7.8 min; $^1$H NMR (300 MHz, CDCl$_3$) 3.63 (t, J=6.6 Hz, 2H, CH$_2$OH), 2.21 (m, 2H, CH$_2$), 1.81 (s, 6H, 2×CH$_3$), 1.78 (s, 3H, CH$_3$), 1.59 (m, 2H, CH$_2$), 1.38 (m, 5H, 2×CH$_2$ and allyl CH), 1.01 (dd, J=7.2, 3.3, 3 H, CH$_3$); GCMS (Trimethylsilyl chloride added) 280.0 (M$^+$+TMS) 7.49 min, 83%.

Example 2

1-(5-Hydroxypentyl)-tetramethylcyclopentadiene (Cp*C$_5$OH), by Grignard Formation

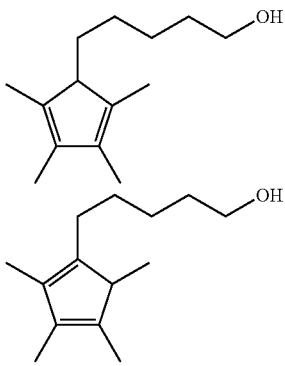

An oven dried three-necked 50 ml round bottom flask with reflux condenser and dropping funnel attached was placed under a nitrogen atmosphere then charged with anhydrous THF (5 ml), magnesium turnings (0.59 g, 24.3 mmol) an one pellet of iodine. 2-Bromo-2-butene (2.3 ml, 22.5 mmol, mixture of cis and trans isomers) was placed in the dropping funnel and a small portion added to the vigorously stirred metal suspension. Once reaction had initiated, evidenced by loss of the iodine colour and refluxing of the solvent, the remaining 2-bromo-2-butene was diluted with THF (10 ml) and added gradually. A cloudy grey solution formed. After complete addition, the reaction mixture was stirred for 1 h at r.t. Caprolactone (1.1 ml, 10.4 mmol) in THF (5 ml) was then added dropwise. After stirring for a further 30 min, the now yellow reaction mixture was quenched by the addition of 20% AcOH aq (10 ml). The organic layer was separated and the aqueous extracted with ether (2×10 ml). The combined ether layers were stirred in a round bottom flask, 10% aqueous hydrochloric acid (20 ml) was added and the two phase mixture stirred for 1.5 h at r.t. The ether layer was separated and the aqueous layer extracted with ether (10 ml). The combined ether layers were washed with sat NaHCO$_3$ aq then water, dried over Na$_2$SO$_4$ and solvent removed to give a pale yellow oil. Purification by eluting through a plug of silica (heptane/EtOAc 4:1 as eluent) gave the product as an almost colourless oil (0.87 g, 40%). HPLC Retention time 7.8 min; GCMS (Trimethylsilyl chloride added) 280.0 (M$^+$+TMS) 7.49 min, 86%.

Example 3

1-(5-Hydroxypentyl)-tetramethylcyclopentadienyl Dichloro Rhodium (III) Dimer [RhCp*C$_5$OHCl$_2$]$_2$

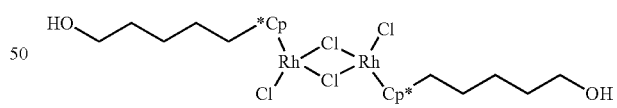

1-(5-Hydroxypentyl)-tetramethylcyclopentadiene (0.40 g, 1.92 mmol) was dissolved in MeOH (4 ml) in a Radleys carousel tube and the solution degassed with nitrogen. Rhodium trichloride hydrate (0.252 g, 0.96 mmol) was added and the reaction mixture heated under nitrogen at reflux for 24 h. After removal of the solvent on a rotary evaporator the red powdery residue was dissolved in a minimum of DCM and product precipitated with heptane and collected by filtration. Repetition of this precipitation process followed by vacuum drying at 40° C. gave product as fine red crystals (0.340 g, 93%). HPLC Retention time 2.8 min; $^1$H NMR (300 MHz, CDCl$_3$) 3.63 (t, J=6.3 Hz, 2H, CH$_2$OH), 2.28 (m, 2H, CH$_2$), 1.64 (s, 6H, 2×CH$_3$), 1.62 (s, 6H, 2×CH$_3$), 1.57 (m, 2H, CH$_2$), 1.41 (m, 4H, 2×CH$_2$).

Example 4

1-(5-Hydroxypentyl)-tetramethylcyclopentadienyl Dichloro Iridium(III) Dimer [IrCp*C₅OHCl₂]₂

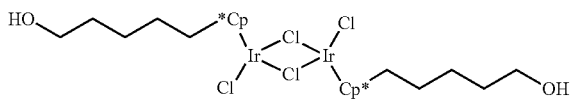

By Conventional Heating 1-(5-Hydroxypentyl)-tetramethylcyclopentadiene (0.20 g, 0.96 mmol) was dissolved in MeOH (4 ml) in a Radleys carousel tube and the solution degassed with nitrogen. Iridium trichloride hydrate (0.16 g, 0.45 mmol) was added and the reaction mixture heated under nitrogen at reflux for 36 h. After removal of the solvent on a rotary evaporator the black residue was dissolved in a minimum of DCM and precipitated with heptane. The heptane was removed, DCM added to the solid and the brown solution separated from a black oily residue. Evaporation of the DCM solution followed by precipitation from DCM with heptane gave the product as an orange solid (0.100 g, 47%). HPLC Retention time 3.2 min.

By Microwave Heating 1-(5-Hydroxypentyl)-tetramethylcyclopentadiene (0.19 g, 0.90 mmol) and sodium bicarbonate (42 mg, 0.5 mmol) were dissolved in MeOH (4 ml) in a 5 ml capacity microwave tube and the solution degassed with nitrogen. Iridium trichloride hydrate (0.16 g, 0.45 mmol) was added and the tube sealed. Microwave heating was applied with a set temperature of 150° C. for 10 minutes. The reaction mixture was diluted with DCM (8 ml) then washed with water (6 ml) and the aqueous layer extracted with DCM (2×4 ml). The combined DCM layers were dried over Na₂SO₄, solvent removed and product precipitated with heptane after dissolution in a minimum volume of DCM. An orange solid was obtained (0.168 g, 79%). HPLC Retention time 3.2 min.

Example 5

1-(5-Hydroxypentyl)-tetramethylcyclopentadienyl Diiodo Iridium(III) Dimer [IrCp*C₅OHI₂]₂

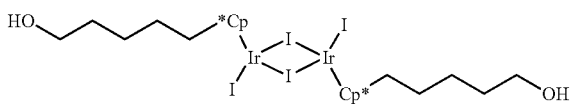

Chloro iridium complex from experiment 4 (69 mg, 0.15 mmol Ir) and sodium iodide (22 mg, 0.60 mmol) were heated at reflux in degassed acetone (2 ml) under a nitrogen atmosphere. After 18 h, the solution was cooled, diluted with DCM (6 ml) and washed with water (6 ml). The aqueous was extracted with DCM (2×2 ml), the combined organic layers dried over Na₂SO₄ and the solvent removed. Product was precipitated with heptane after dissolution in a minimum volume of DCM to give a brick red crystalline solid, 75 mg (77%). Single crystal x-ray diffraction confirmed the identity of this structure.

Example 6

Attachment to Quadrapure™ Resin

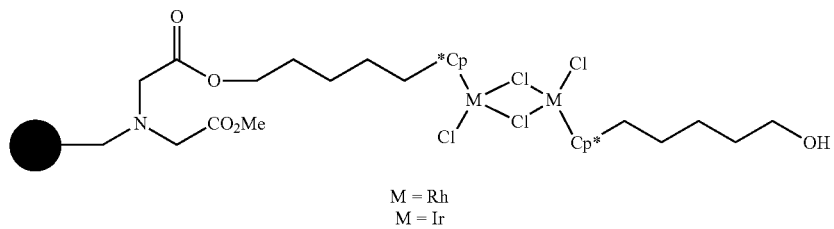

M = Rh
M = Ir

Ligands were attached to Quadrapure™ IDA resin by diisopropylcarbodiimide, carbonyldiimidazole or thionyl chloride activation according to the following procedures.

Diisopropylcarbodiimide Activation

Quadrapure IDA beads (1.05 g, 7 mmol) were suspended in DCM (10 ml), diisopropylcarbodiimide (1.2 ml, 7.7 mmol) in DCM (5 ml) was added and the reaction mixture stirred for 20 min at 40° C. Rhodium complex [RhCp*C₅OHCl₂]₂ of example 3 (76.1 mg, 0.2 mmol Rh) in DCM (4 ml) was added followed by DMAP (86 mg, 0.7 mmol) and stirring continued for a further 18 h. MeOH (1 ml) was added to quench unreacted resin sites and after an additional 1 h at 40° C. the beads were collected on a sinter (filtrate yellow), washed with DCM (2×10 ml), MeOH (2×10 ml) then DCM (4×10 ml). Vacuum drying gave pale orange beads of the rhodium supported complex Carbonyldiimidazole Activation Quadrapure IDA beads (1.08 g, 7 mmol) were suspended in DCM (5 ml), carbonyldiimidazole (1.25 g, 7.7 mmol) in DCM (3 ml) was added and the reaction mixture stirred for 15 min at r.t. Rhodium complex [RhCp*C₅OHCl₂]₂ of example 3 (38 mg, 0.1 mmol Rh) in DCM (2 ml) was added and stirring continued for a further 20 min after which time MeOH (1 ml) was added to quench unreacted resin sites. The beads were collected on a sinter (filtrate yellow), washing with DCM (4×10 ml) then vacuum dried to give beads close in colour to the starting material.

Thionyl Chloride Activation

Quadrapure IDA beads (1.01 g, 7 mmol) were suspended in DCM (10 ml), thionyl chloride (2.6 ml, 70 mmol) was added and the reaction mixture stirred for 1 h at 40° C. The beads were filtered on a sinter and washed with DCM (5×10 ml), before being resuspended in a round bottom flask in DCM (10 ml). Rhodium complex [RhCp*C₅OHCl₂]₂ of example 3 (76.1 mg, 0.2 mmol Rh) in DCM (4 ml) containing N-diisopropylethylamine (1.2 ml, 14 mmol) was added and the reaction mixture stirred at 40° C. for 18 h. MeOH (1 ml) was added to quench unreacted resin sites and after an additional 1 h at 40° C. the beads were collected on a sinter (filtrate yellow), washed with DCM (2×10 ml), MeOH (2×10 ml) then DCM (4×10 ml). Vacuum drying gave pale orange beads of rhodium supported immobilised.

Example 7

Attachment to 2-Chlorotrityl Resin

Rhodium complex [RhCp*C$_2$OHCl$_2$]$_2$ of example 3 (77.6 mg, 0.2 mmol Rh) was dissolved in DCM (4 ml) and N-diisopropylethylamine (0.52 ml) added. This solution was added to an oven dried flask containing 2-chlorotrityl chloride resin (1.007 g, 1 mmol), washing in with a further portion of DCM (2 ml). The flask was flushed with nitrogen, stoppered and incubated at 35-37° C. for 24 h. The resin was collected by filtration and washed with DCM (5 times) then quenched with 10% N-diisopropylethylamine in MeOH before further washes with DCM (10 times) and MeOH (5 times). The resin was vacuum dried to yield dark red beads of rhodium supported complex.

Example 8

Use of Supported Catalysts in a Transfer Hydrogenation Reaction

Supported catalysts of Examples 6 and 7 were used to catalyse the transfer hydrogenation of 6,7-dimethoxy-1-methyl-3,4-dihydroisoquinoline. As FIG. 1 illustrates, the supported catalysts gave an equivalent enantiomeric excess (ee) to the homogeneous catalyst. No leaching of coloured metal species was observed from the supported catalyst and a second use of the beads gave essentially the same enantiomeric excess.

The invention claimed is:

1. A metal complex comprising a metal and one or more ligands, wherein the metal is selected from the group consisting of rhodium, iridium, platinum, palladium, titanium, ruthenium and cobalt and at least one of the ligands is a compound of the formula (I):

$$R^1\diagdown_X\diagup^Y \quad (I)$$

wherein
R$^1$ is a cyclopentadienyl group;
X is an alkylene linker comprising at least two in-chain carbon atoms; and Y is selected from the group consisting of =O, —OH, =S, —SH, —S(O), —S(O)$_2$, NH$_2$, amino or mono-substituted amino.

2. The metal complex according to claim 1, wherein the compound is not selected from the group consisting of 1-(3-hydroxypropyl)-2,3,4,5-tetramethylcyclopentadiene, 1-(4-hydroxy butyl)-2,3,4,5-tetramethylcyclopentadiene, 1-(5-hydroxypentyl)-2,3,4,5-tetramethylcyclo pentadiene, 1-(3-aminopropyl)-2,3,4,5-tetramethytcyclopentadiene, 1-(4-aminobutyl)-2,3,4,5-tetramethylcyclopentadiene, 1-(5-aminopentyl)-2,3,4,5-tetramethylcyclopentadiene and 1-(8-heptadecenyl)2,3,4,5-tetramethylcyclopentadiene.

3. The metal complex according to claim 1, wherein R$^1$ is tetramethylcyclopentadienyl.

4. The metal complex according to claim 1, wherein X has 2 to 20 in-chain carbon atoms.

5. The metal complex according to claim 1, wherein X is an alkenylene group.

6. The metal complex according to claim 2, wherein Y is selected from the group consisting of =O, —OH and —NH$_2$.

7. The metal complex according to claim 1, wherein Y is a mono-substituted amino group.

8. The metal complex according to claim 7, wherein the amino group is substituted with a substituted C$_{1-6}$ alkyl, aryl, arylalkyl or heteroaryl group.

9. The metal complex according to claim 7, wherein the mono-substituted amino group is N—(C$_{1-6}$ alkyl)amino, amino or tosyl amino.

10. The metal complex according to claim 1, wherein the X and/or Y is selected from the group consisting of 2-hydroxyethyl, 3-hydroxy-n-propyl, 4-hydroxy-n-pentyl, 2-hydroxypropyl, 3-hydroxybutyl, 3-hydroxy-1-methylpropyl, 1-methylene-3-hydroxypropyl, 3-hydroxy-3-phenylpropyl, 2-oxopropyl, 3-oxobutyl, 4-oxopentyl, 3-aminopropyl, 5-aminopentyl, 3-propanoate and 5-pentanoate.

11. The metal complex according to claim 1, wherein the metal is a transition metal.

12. The metal complex according to claim 1, wherein the metal is rhodium or iridium.

13. The metal complex according to claim 1, wherein the metal complex comprises one or more additional ligands.

14. A process for production of a metal complex comprising a metal and one or more ligands, the metal is selected from the group consisting of rhodium, iridium, platinum, palladium, titanium, ruthenium and cobalt and at least one of the ligands is a compound of formula (I):

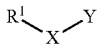

wherein
R¹ is a cyclopentadienyl group;
X is an alkylene linker comprising at least two in-chain carbon atoms; and
Y is selected from the group consisting of =O, —OH, =S, —SH, —S(O), —S(O)$_2$, amino and mono-substituted amino, wherein the process comprises
i) contacting a compound of formula (III):

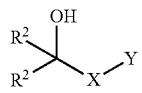

wherein
X is an alkylene linker comprising at least two in-chain carbon atoms;
Y is selected from the group consisting of =O, —OH, =S, —SH, —S(O), —S(O)$_2$, amino and mono-substituted amino;
each R² is independently an ethenyl group;
with an acid under conditions such that the R² groups and the carbon atom to which they are attached together form a cyclopentadienyl group; and
ii) contacting the compound of formula (I) with a metal to form the metal complex.

15. The metal complex according to claim 1, further comprising a catalyst.

16. The metal complex according to claim 7, wherein the amino group is substituted with a hydrocarbyl group, a heterocyclyl group or a heterocycloalkyl group.

17. The metal complex according to claim 16, wherein the hydrocarbyl group, heterocyclyl group or heterocycloalkyl group are optionally attached to the nitrogen atom of the amino group via a linkage selected from the group consisting of —O—, C(O)—, —C(O)O—, —S—, —S(O)— and —S(O)$_2$—.

* * * * *

UNITED STATES PATENT AND TRADEMARK OFFICE
CERTIFICATE OF CORRECTION

Page 1 of 1

PATENT NO. : 8,865,924 B2
APPLICATION NO. : 13/912508
DATED : October 21, 2014
INVENTOR(S) : John Blacker et al.

It is certified that error appears in the above-identified patent and that said Letters Patent is hereby corrected as shown below:

In the Claims

Column 14, Line 47, Claim 9:

After "mono-substituted amino group is N-($C_{1-6}$ alkyl)amino," insert -- acetyl --

Signed and Sealed this
Tenth Day of March, 2015

Michelle K. Lee
*Deputy Director of the United States Patent and Trademark Office*